United States Patent
Paul et al.

(10) Patent No.: US 6,299,837 B1
(45) Date of Patent: Oct. 9, 2001

(54) PROCEDURE TO PRODUCE A DISINFECTING HOT ATMOSPHERE AND DEVICE TO ACCOMPLISH THIS

(75) Inventors: Elke Paul, Münster; Waldemar Pieczarek, Bruchköbel; Hubert Heeg, Mömbris, all of (DE)

(73) Assignee: Kendro Laboratory Products GmbH, Hanau (DE)

( * ) Notice: Subject to any disclaimer, the term of this patent is extended or adjusted under 35 U.S.C. 154(b) by 0 days.

(21) Appl. No.: 09/211,733

(22) Filed: Dec. 15, 1998

(30) Foreign Application Priority Data

Dec. 16, 1997 (DE) .............................................. 197 55 668

(51) Int. Cl.$^7$ ...................................................... A61L 2/08
(52) U.S. Cl. ................................ 422/26; 422/21; 422/26; 422/298; 422/299; 422/300; 422/307
(58) Field of Search ............................... 422/21, 26, 298, 422/299, 300, 307

(56) References Cited

U.S. PATENT DOCUMENTS

| | | | |
|---|---|---|---|
| 4,039,775 | | 8/1977 | Amdra ................................. 219/385 |
| 4,336,329 | | 6/1982 | Hesse et al. ............................. 435/3 |
| 4,447,399 | * | 5/1984 | Runnells et al. ...................... 422/299 |
| 4,685,507 | * | 8/1987 | Schafer ................................ 422/299 |
| 4,716,676 | * | 1/1988 | Imagawa ................................ 422/26 |
| 5,019,344 | * | 5/1991 | Kutner et al. ........................... 422/21 |
| 5,309,981 | | 5/1994 | Binder ................................... 265/64 |

FOREIGN PATENT DOCUMENTS 44 06 632 C1    1/1994 (DE) .

* cited by examiner

Primary Examiner—Robert J. Warden, Sr.
Assistant Examiner—Imad Soubra
(74) Attorney, Agent, or Firm—Workman, Nydegger & Seeley

(57) ABSTRACT

A gassing incubator includes an inner housing bounding a inside space. The inside space communicates to the exterior through an opening. The opening is selectively sealed closed by a movable door. The inner housing includes a floor which is configured to receive and retain water. To disinfect the inside space, water is disposed on the floor and the opening is sealed closed. The inside space is then heated to a disinfecting temperature of about 90° C. The water is also heated so as to produce a relative humidity of greater than about 80% within the inside space. This atmosphere is maintained for a disinfection phase of at least 9 hours. The hot and humid atmosphere of the inside space produces great heat sensitization of cells which might be present. As a result, substantially all of the cells within the inside space are killed during the 9-hour disinfection phase. Before the subsequent initial operation of the gassing incubator, there follows a condensation phase to reduce the relative humidity within the inside space, and a cooling and post-heating phase.

12 Claims, 2 Drawing Sheets

US 6,299,837 B1

PROCEDURE TO PRODUCE A DISINFECTING HOT ATMOSPHERE AND DEVICE TO ACCOMPLISH THIS

This application claims priority under 35 U.S.C. §119 to German patent application number 197 55 688.4, filed Dec. 16, 1997, which for purposes of disclosure is incorporated herein by specific reference.

BACKGROUND OF THE INVENTION

1. The Field of the Invention

The present invention relates to apparatus and procedures for producing a disinfecting hot atmosphere within the inside space of a gassing incubator. More specifically, the present invention relates to supplying a quantity of water within the inside space of a gassing incubator and heating the atmosphere and the surfaces of the inside space in a heat-up phase (I) after the inside space is sealed to the surrounding atmosphere.

2. Present State of the Art

German Patent No. 44 06 632 C1 ("the '632 patent") discloses a solids bioreactor for culturing microorganisms on solid, particulate substrates. The '632 patent discloses regulating the temperature between $-27$ and $+100°$ C., and the relative humidity from 40–99% using cold water vapor produced by ultrasound. The invention produces a directional forced flow of the gas atmosphere whose composition can be metered (the oxygen content is adjustable from 0 to 100% in the mixture with nitrogen, carbon dioxide, and possibly other gases) and whose volume flow can be adjusted. The '632 patent also discloses devices for superheated steam sterilization of the bioreactor and devices to carry off and sterilize the condensate and exhaust air.

One of the problems with the invention disclosed in the '632 patent is that proper superheated steam sterilization requires an additional unpressurized superheated steam supply or an additional connection to such a supply.

German Patent No. 29 24 446 C2 ("the '446 patent") also discloses a procedure for cultivating cells and tissues of humans and animals or microorganisms by means of containers which are put in an incubator. The incubator is gassed in a controlled manner with carbon dioxide, air, or oxygen or nitrogen, and the atmosphere thereof is humidified and kept at a specified temperature. In this process, the gases are fed, individually or together, through a sterilization filter within the line in the incubator's double-walled jacket to a by-pass canal. The gasses are then mixed with water vapor from the line. The water vapor is sterilized by superheating in the evaporator outside the useful space and then cooled. A controller for the relative humidity keeps the humidity in the range from about 60 to 95 percent. This means that the relative humidity can be adjusted not only close to the saturation limit, but can also be adjusted in the broad range from 60 to 95 percent. The useful space and/or by-pass, including the probe, can be sterilized by baking up to 180° C. with a heater associated with the useful space.

One of the problems with the invention of the '466 patent is the relatively high disinfection temperature. Specifically, the high disinfection temperature can detrimentally affect temperature-sensitive components, such as, for example, sensors, seals, or recirculation devices.

OBJECTS AND BRIEF SUMMARY OF THE INVENTION

One of the objects of the present invention is to specify a procedure and/or a device for effective sterilization, especially in the empty inside space of a gassing incubator, which avoids the high temperatures commonly used in high-humidity disinfection.

To achieve the foregoing objects, and in accordance with the invention as embodied and broadly described herein, a process is provided which includes feeding water to form water vapor within a chamber such as in a gassing incubator. Once the atmosphere of water vapor reaches a temperature of 90° C. and a relative humidity of more than 80%, the atmosphere of water vapor is maintained for a disinfection phase (II) of at least 9 hours. The high-humidity atmosphere according to the present invention produces greater heat sensitization of the unwanted cells within the chamber than that produced by a dry atmosphere. The present invention thus has the advantage that practically all of the cells can be thermally killed in the nine-hour disinfection phase.

In a one embodiment of the present invention, a quantity of at least 300 ml of water is put into an inside space of a chamber having a volume ranging from about 15 liters to about 400 liters, with about 150 liters being more preferred. Next, heat is fed through substantially all the surfaces bounding the inside space so as to reach a desired disinfection temperature.

It is advantageous for the disinfection process to take place automatically, achieving a decontamination which includes all fixtures and sensors within the inside space. It is also advantageous that the disinfection procedure be performed in an atmosphere whose pressure differs only negligibly from the surrounding atmosphere.

In one embodiment, the above objectives and process steps are achieved by a gassing incubator with a heatable inside space. The inside space is in part bounded by a floor area configured for holding fluid. At least one temperature stabilization element is disposed at the floor area and in at least one of the side walls and/or ceiling area bounding the inside space. The temperature stabilization elements in the floor area are separately controlled from the other stabilization elements.

One of the advantageous of the present invention is that relatively low temperatures are used which produce a substantially lower material load on the inside space than known procedures. Another advantage of the present invention is that the pressure within the inside space does not have to be substantially higher than that of the surrounding atmosphere. As a result, the possible sealing problems resulting from different inside and outside pressures is substantially eliminated.

In one embodiment, the temperature stabilization elements associated with the floor area consist of heating and/or cooling elements. The present invention thus provides the advantage that both a rapid heating phase and a relatively short condensation phase can be achieved.

In another embodiment of the present invention, the inside space has a front-side opening which can be sealed gas-tight by an inside door. The temperature of the inside door can be stabilized to prevent condensation thereon. The inside door can also be made to be at least partially transparent.

It is an advantage of the present invention that possible condensation on the inside door and on the walls of the inside space is prevented, to as great an extent possible, from reaching dry surfaces of the walls, ceiling, and inside door. That is, it is another objective of the present invention to provide a dry surface on some or all of the side walls, back wall, ceiling area, and inside door bounding the inside space after sterilization in order to prevent accidental contact and contamination by an operator of a wet surface of the inside space. This is accomplished by heating the various surfaces, except the floor, bounding the inside space after sterilization.

The inside space includes a useful space which is the actual space available for holding the material to be processed. The inside space also includes its periphery as well as, e.g., a fan and the area covered by water on the floor.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
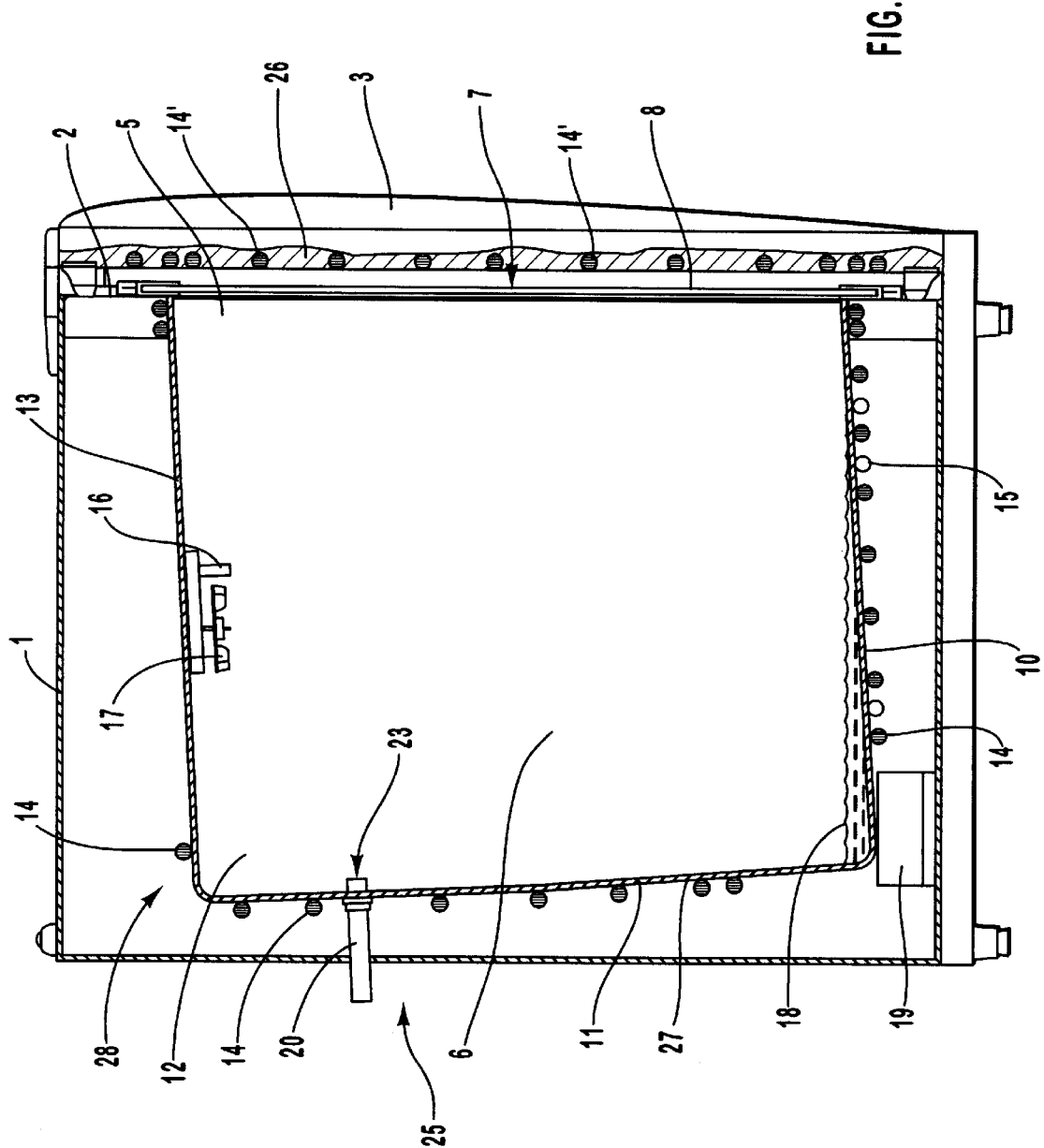
FIG. 1 is a cross-sectional side view of a gassing incubator having a useful space.

Disclosed in FIG. 1 is one embodiment of an inventive gassing incubator 25 incorporating features of the present invention. Gassing incubator 25 includes an outer housing 1 bounding an interior space 28. Outer housing 1 includes a front side 2 having an opening 26 formed thereat. Opening 26 is selectively closed by means of an outside door 3 mounted on outer housing 1.

Disposed within interior space 28 is an inner housing 27 which bounds a inside space 5. Inner housing 27 includes a floor area 10, a back wall 11, opposing side walls 12, and a ceiling area 13. Inside space 5 communicates with the exterior through an opening 7 which is aligned with opening 26. Opening 7 is selectively closed by means of a transparent inside door 8 which has a sealing function.

Heating elements 14 are disposed at floor area 10, back wall 11, opposing side walls 12, and ceiling area 13. In one embodiment, each heating element 14 is disposed between outer housing 1 and inner housing 27 such that heating elements 14 are distributed in close thermal contact over the corresponding wall, floor, or ceiling area. In one embodiment, heating elements 14 can be individually controlled or controlled as groups to selectively heat different surfaces. That is, the temperature of floor area 10, back wall 11, opposing side walls 12, and ceiling area 13 can be individually controlled. Cooling elements 15 can similarly be disposed at floor area 10. Heating elements 14' can also be positioned on outside door 3 for selective heating of inside door 8 when both doors 3 and 8 are closed. In an alternative embodiment, a glass light mounted on inside door 8 can be used for heating inside door 8. Disposed with inside space S is a temperature sensor 16 and a fan 17. In one embodiment, sensor 16 and fan 17 are mounted on ceiling area 13.

In the embodiment depicted, floor area 10 includes a reservoir tub-like form 18 configured to receive and retain water. The water poured therein provides the humidity necessary for the disinfection procedure.

Inside space 5 includes a useful space 6. Useful space 6 is that area within inside space 5 in which samples can be disposed for treatment. For example, useful space 6 does not include floor area 10 covered by water since the water could damage the samples. Likewise, useful space 6 does not include the area that is directly in the path of fan 17.

An opening 23 formed in back wall 11 is selectively closed by a filter plug 20. Filter plug 20 functions to provide pressure equalization between the atmosphere inside useful space 6 and the surrounding atmosphere. As a result, there is practically no pressure difference between useful space 6 and the surrounding atmosphere.

Figure 2:
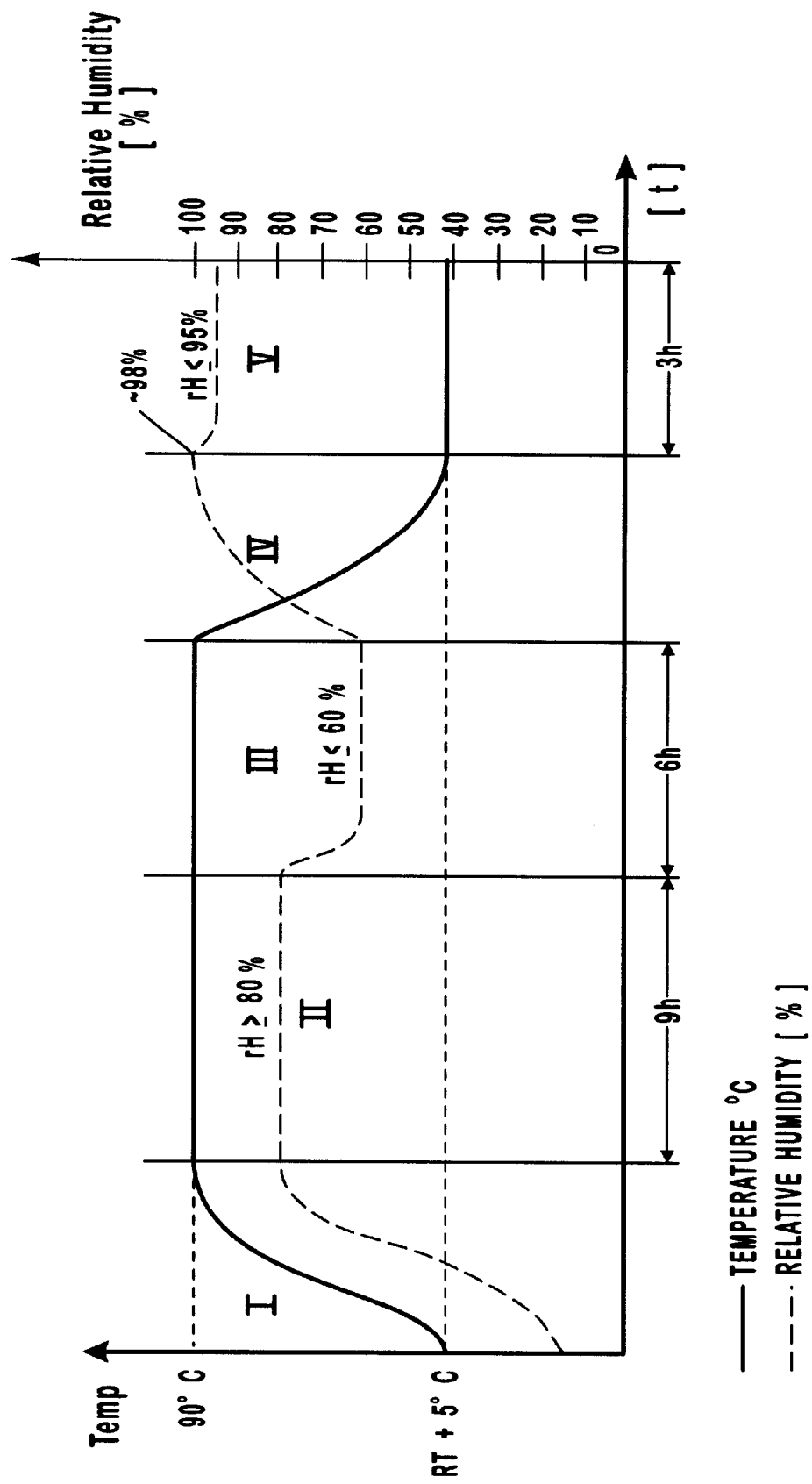
FIG. 2 is a plot of temperature and relative humidity against time showing the different phases for disinfection and initial operation of the useful space shown in FIG. 1.

Before commencing the disinfection process, whose progression is shown in detail in FIG. 2, gassing incubator 25 is shut off, any culture material which might be present is removed from inside space 5, and water reserve 18 is emptied. The surfaces bounding inside space 6 can then be manually cleaned.

The disinfection procedure per se is explained in detail using the five phases I through V in the plot of temperature and relative humidity against time as shown in FIG. 2. The time axis "t" is divided into phases I, II, III, IV, and V. Each phase has a corresponding time interval designated by hours (h). The temperature axis "Temp." is in degrees Celsius. The relative humidity axis is in percent %.

Initially, floor area 10, shown in FIG. 1, is filled up with water. For example, floor area 10 can be fill with about 300 ml of water for an inside space having a volume of about 150 liters. Next, heat-up phase I is accomplished by raising the atmospheric temperature within useful space 6. In one example, the temperature is raised from room temperature "RT"+5° C. (approximately 37° C.) to a disinfection temperature of 90° C. Heating the atmosphere within useful space 6 is accomplished by activating heating elements 14 which are mounted against floor area 10, back wall 11, opposing side walls 12, and ceiling area 13. Heating element 14' on outside door 3 can also be activated. In alternative embodiments, select heating elements 14 at different locations can be activated.

As a result of heating floor area 10, the water retained on floor area 10 is converted into water vapor within useful space 6. As a result, after the desired temperature of about 90° is reached, the relative humidity within useful space 6 is greater than about 80%. The duration of heat-up phase I depends on the surrounding temperature, the device being heated up, and the heating capacity.

After the desired temperature of 90° C. is reached, the disinfection process per se begins. The disinfection process is designated as phase II and typically extends for about nine hours. During phase II, the high atmospheric humidity within useful space 6 causes great heat sensitization of the cells which are present within useful space 6. Thus, during the nine-hour disinfection phase II, cells or bacteria which are within useful space 6 are subject to great thermal conductivity. As a result, the nine-hour disinfection phase II kills practically all cells. The actual duration of the disinfection phase II, which is the phase of cell killing, depends on the procedure.

Following phase II is an approximately six-hour condensation phase designated in FIG. 2 as phase III. During phase III, the relative humidity of more than 80% produced within useful space 6 during phase II is reduced. To accomplish this, heating elements 14 against floor area 10, as shown in FIG. 1, are turned off. In one embodiment, cooling elements 15 at floor area 10 are activated. Cooling floor area 10 condenses the water vapor in the atmosphere of useful space 6 at least enough so that after condensation phase III is completed, the relative humidity still within useful space 6 is less than about 60 percent. A simplified form of gassing incubator 25 can do without cooling elements 15. Typically, at least part of the remaining heating elements 14 not at floor area 10 remain activated so that the atmospheric temperature within useful space 6 remains substantially the same during phase III as in phase II.

Condensation phase III is followed by a cooling phase IV. During cooling phase IV, the atmospheric temperature of useful space 6 is cooled from the desired value for disinfection (90° C.) to the value planned for the later operation of the gassing incubator, for example, 37° C. For this purpose, the normal heating elements 14 for the useful space are turned off. The one exception is that heating elements 14' for transparent inside door 8 (glass door) which closes opening 7 is still being heated to prevent condensation on inside door 8. The duration of the cooling phase IV ranges from 4 to 5 hours, depending on the surrounding temperature.

Following cooling phase IV is a post-heating phase indicated with V in FIG. 2. Gassing incubator containing wet inside walls keeps a high risk that the wet surfaces of the inside walls might be touched and thereby contaminated during a new charging process after sterilization. It is thus a useful feature of the present invention to obtain clean and dry walls of inside space 5, except for floor area 10, by post-heating phase V. During phase V, which for example can last for about 3 hours, condensation which might appear on the inside door 8 and the walls of the inside space is eliminated to prevent it from reaching the dry surfaces of the wall, ceiling, and glass door. Specifically, during phase V heating elements 14 at back wall 11, opposing side walls 12, and ceiling area 13 are turned on and raised to a temperature above the dew point. Heating element 14' remains on from during phase IV. Thus it is possible to obtain dry surfaces on back wall 11, opposing side walls 12, ceiling area 13, and inside door 8 by evaporation of any condensation on the surfaces. The duration of phases IV and V depends on the device being used.

The disclosed invention is advantageous in that the procedure as shown in FIG. 2 achieves a decontamination which includes all internal fixtures and sensors within useful space 6. The disclosed decontamination process is also advantageous because the disinfection procedure is carried out in an atmosphere whose pressure corresponds as closely as possible to that of the surrounding atmosphere. The disinfection process is also automatically timed and thermostatically controlled.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A procedure for disinfecting a gassing incubator having an inside space, the procedure comprising:
    (a) positioning a free standing pool of water within the inside space of the gassing incubator;
    (b) sealing the inside space so as to be substantially closed to the surrounding atmosphere;
    (c) heating the atmosphere within the inside space to a disinfecting temperature;
    (d) heating the free standing pool of water within the inside space to a temperature sufficient to produce a relative humidity of at least about 80% within the inside space;
    (e) maintaining the disinfecting temperature and the relative humidity of at least about 80% within the inside space for a sufficient period of time to produce disinfecting; and
    (f) substantially maintaining the disinfecting temperature within the atmosphere of the inside space while cooling the free standing pool of water within the inside space so that the relative humidity within the inside space is decreased.

2. A procedure as recited in claim 1, wherein the disinfecting temperature and the relative humidity of at least about 80% is maintained within the inside space for a period of at least about 9 hours.

3. A procedure as recited in claim 1, wherein the step of heating the atmosphere within the inside space includes the disinfecting temperature being at least about 90° C.

4. A procedure as recited in claim 1, wherein the free standing pool of water within the inside space is cooled so that the relative humidity within the inside space is decreased by at least 20%.

5. A procedure according to claim 4, wherein the housing includes a floor on which the water is received and retained, wherein the step of cooling the water within the inside space comprises cooling the floor.

6. A procedure as recited in claim 1, wherein the atmospheric pressure within the inside space is maintained substantially the same as the outside surrounding atmospheric pressure during the step of heating the atmosphere within the inside space to a disinfecting temperature.

7. A procedure according to claim 1, wherein the housing includes a floor, a back wall, a pair of opposing side walls, and a ceiling, wherein the step of heating the atmosphere within inside space includes heating at least one of the back wall, the pair of opposing side walls, and the ceiling from outside of the inside space.

8. A procedure for disinfecting a gassing incubator, the procedure comprising the steps of:
    (a) positioning a free standing pool of water on the floor of an inner housing of the gassing incubator, the inner housing having an interior surface bounding an inside space;
    (b) activating a first heating element communicating with the floor and a second heating element communicating with the inner housing separate from the floor so as to produce an atmosphere within a portion of the inside space having an elevated first temperature and an elevated first relative humidity;
    (c) maintaining the atmosphere within the inside space at the elevated first temperature and the elevated first relative humidity for a time period sufficient to disinfect the interior surface of the inner housing exposed to the atmosphere; and
    (d) decreasing the temperature of the first heating element to a temperature below the temperature of the second heating element so that the free standing pool of water on the floor of the inner housing is cooled, thereby decreasing the relative humidity within the atmosphere to a second relative humidity.

9. A procedure as recited in claim 8, wherein the act of decreasing the temperature of the first heating element is accomplished while substantially maintaining the first temperature of the atmosphere.

10. A procedure as recited in claim 9, further comprising the steps of:
(a) turning off the second heating element so as to lower the temperature of the atmosphere to a desired operating temperature; and
(b) turning on the second heating element after the atmosphere has been lowered to the desired operating temperature so as to evaporate condensation off at least a portion of the interior surface of the inner housing.

11. A procedure as recited in claim 8, wherein the cooling step comprises turning off the first heating element.

12. A procedure for disinfecting a gassing incubator having an inside space, the procedure comprising the steps of:

(a) positioning a free standing pool of water within the inside space of the gassing incubator;
(b) sealing the inside space so as to be substantially closed to the surrounding atmosphere;
(c) heating the atmosphere within the inside space to a disinfecting temperature of at least about 90° C.;
(d) heating the pool of water within the inside space to a temperature sufficient to produce a relative humidity of at least about 80% within the inside space; and
(e) maintaining the disinfecting temperature of at least about 90° C. and the relative humidity of at least about 80% within the inside space for at least about 9 hours so as to disinfect the useful space.

* * * * *